United States Patent [19]

Sih

[11] Patent Number: 4,751,182

[45] Date of Patent: Jun. 14, 1988

[54] PROCESS FOR PREPARING L-CARNITINE FROM DL-CARNITINE

[75] Inventor: Charles I. Sih, Madison, Wis.

[73] Assignee: Wisconsin Alumni Research Foundation, Madison, Wis.

[21] Appl. No.: 803,372

[22] Filed: Dec. 2, 1985

Related U.S. Application Data

[63] Continuation-in-part of Ser. No. 602,289, Apr. 20, 1984, abandoned.

[51] Int. Cl.[4] .................. C12P 13/00; C12P 41/00; C12N 1/20; C12R 1/01
[52] U.S. Cl. .................. 435/128; 435/172.1; 435/253; 435/822; 435/280
[58] Field of Search .............. 435/128, 253, 172.1, 435/280, 822

[56] References Cited

U.S. PATENT DOCUMENTS

| | | | |
|---|---|---|---|
| 3,600,279 | 8/1971 | Takahashi et al. | 435/280 |
| 3,912,592 | 10/1975 | Makover et al. | 435/881 |
| 4,209,507 | 6/1980 | Ogino et al. | 435/822 |
| 4,217,411 | 8/1980 | Le Frock et al. | 435/34 |
| 4,221,869 | 9/1980 | Vandecasteele et al. | 435/117 |
| 4,371,618 | 2/1983 | Cavazza | 435/128 |

OTHER PUBLICATIONS

G. Fraenkel & S. Friedman, *Vitam, Horm.*, (N.Y.), 1957, 16,73.
J. Miura-Fraboni & S. England, *Fems Microbiology Lett.*, 18, 1983), 113.
H. P. Kleber et al., *Arch. Microbiology* 112, (1977), 201.

*Primary Examiner*—Elizabeth Weimar
*Attorney, Agent, or Firm*—Howard W. Bremer

[57] ABSTRACT

This invention relates to a process for resolving DL-carnitine by contacting a racemic mixture of DL-carnitine with a microorganism which preferentially metabolizes D-carnitine and permits accumulation of L-carnitine in the reaction medium and to novel strains of such microorganisms and mutants of such strain.

36 Claims, No Drawings

PROCESS FOR PREPARING L-CARNITINE FROM DL-CARNITINE

This application is a continuation-in-part of application Ser. No. 602,289, filed Apr. 20, 1984, now abandoned.

TECHNICAL FIELD

This invention relates to a process for preparing L-carnitine.

More specifically, this invention relates to a process for preparing L-carnitine by fermentation means.

Still more specifically, this invention relates to a process for resolving DL-carnitine microbiologically.

This invention also relates to novel microorganisms which can be used to resolve DL-carnitine.

BACKGROUND ART

It is well documented that a variety of microorganisms are capable of utilizing L-carnitine as a sole carbon source. For example, it was reported that a bacterium (tentatively identified as a Pseudomonad), isolated from a polluted stream bed, utilized L-caritine from a DL-mixture to produce D-carnitine in high optical yield [G. Fraenkel and S. Friedman, *Vitam. Horm.* (N.Y.) 1957 16, 73]. Subsequently, the metabolism of D- and L-carnitine by resting cells of *Pseudomonas putida* and *Acinetobacter calcoaceticus* was investigated. Cells of *Ps. putida* grown on DL-carnitine degraded only L-carnitine with stoichiometric accumulation of glycine betaine [J. Miura-Fraboni and S. Englard, *FEMS Microbiology Lett.* 18 (1983) 113]. Some apparent controversy exists relative to the metabolism of carnitine by *A. calcoaceticus*. One report stated that this organism grew only on L-carnitine with the formation of trimethylamine [H. P. Kleber et al., *Arch. Microbiol.* 112 (1977) 201]. D-carnitine was metabolized, if an additional carbon source, like L-carnitine, was present in the incubation mixture, or if the bacteria were preincubated with L- or DL-carnitine, but no growth was observed on D-carnitine as the sole carbon source. On the other hand, J. Miura-Fraboni and S. England claimed that *A. calcoaceticus* utilized for growth both the D- and L-isomers of carnitine as sole carbon source with stoichiometric formation of trimethylamine, but, until the present invention no microorganisms have been reported which, in an incubation mixture containing DL-carnitine, preferentially degrade the unnatural form of carnitine, D-carnitine, resulting in the accumulation of the desired natural L-carnitine in the medium.

Also of interest is U.S. Letters Pat. No. 4,209,507 Ogino et al. which reports a variant strain of *Acinetobacter Calcoaceticus* var. microformis SC-1714 (ATCC-31299) from the culture of which in a suitable medium is derived a substance showing certain antitumor activity. Applicant has found that the Ogino et al. variant is ineffective to produce L-carnitine in accordance with the process of the present invention.

DISCLOSURE OF THE INVENTION

It has now been found that a racemic mixture of DL-carnitine can be resolved by subjecting it to the fermentative action of enzymes elaborated by microorganisms which are characterized by their unique ability to preferentially metabolize the unnatural D-form of the compound, thereby permitting the desired, natural, L-carnitine to accumulate in the reaction medium from which the L-carnitine can be readily recovered. This process can be represented schematically as follows:

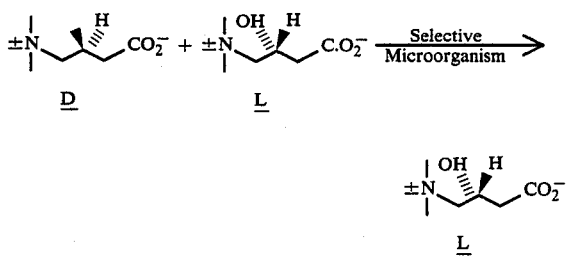

A wild strain of *A. calcoaceticus* which has the unique characteristic referred to above has been isolated from sewage. Whereas known strains of microorganisms that will metabolize carnitine will not function to resolve DL-carnitine since they metabolize D- and L-carnitine at equal rates, this wild strain which has the charateristics of ATCC 39648, is characterized by its ability to metabolize D-carnitine at a faster rate than L-carnitine in liquid or solid media. Thus, this strain responds to the criteria required of a microorganism for purposes of the process of the present invention and has the unique ability to resolve DL-carnitine and permit recovery of the natural and desired form of carnitine, L-carnitine.

In addition to the above identified wild strain, a mutant of that strain, which has the characteristics of ATCC 39647, has been prepared. This mutant is distinguished from the wild strain by its ability to permit the accumulation of greater quantities of L-carnitine in the reaction medium when utilized to resolve DL-carnitine through fermentative action.

The mutant, ATCC 39647, can be obtained by growing *A. calcoaceticus* ATCC 39648 on a suitable medium containing DL-carnitine and then subjecting it to nitrosoguanidine (NTG) mutagenesis. The mutant is then selected on agar plates containing either D- or L-carnitine as the sole carbon source. The desired mutant *A. calcoaceticus* ATCC 39647 will grow poorly on a medium containing L-carnitine as the sole carbon source but will grow rapidly on plates containing D-carnitine as the sole carbon source. This selection was achieved by the replica plating method [D. F. Spooner and G. Sykes in *Methods in Microbiology*, Vol. 7B, p. 244 (1972)]. It will be evident to those skilled in the art that other mutation procedures may be successfully utilized to produce mutants suitable for the process of this invention. Thus, instead of using nitrosoguanidine to achieve mutagenesis other chemical mutagens can be employed such as, for example, sodium nitrite, ethyleneimine, 8-azaguanine, N-methyl N'-nitrosoguanine or nitrogen mustards followed by selection. In addition, physical mutagenesis may be employed utilizing UV light and ionizing or high energy radiation such as X-rays, gamma rays and electron beams. Mutagenesis may also be accomplished through presently available molecular biology techniques, e.g. transduction, transformation, conjugation, cell fusion, recombinant DNA techniques to engineer new microorganism strains.

The strains of *A. calcoaceticus* which have the characteristic of ATCC 39647 and ATCC 39648 have been deposited with the American Type Culture Collection, 12301 Parklawn Drive., Rockville, Md. 20852 and are maintained under the provisions of the Budapest Treaty for the Deposit of Microorganisms.

BEST MODE FOR CARRYING OUT THE INVENTION

The preferred process of the present invention comprises cultivating a microorganism having the identifying characteristics of *A. calcoaceticus* ATCC 39647 in an aqueous nutrient medium under aerobic conditions in a mineral salts medium containing DL-carnitine as the sole carbon source. Alternatively, the DL-carnitine can be added to the microorganism culture after it has been grown on a nutrient medium.

The preferred concentration of the DL-carnitine (as hydrochloride) is about 0.1 to about 100 grams per liter, depending upon the ratio of DL-carnitine and the ammonia concentration of the medium. It will be understood that with increasing DL-carnitine chloride concentrations, more ammonium ion is required to achieve the optimum rate of metabolism of the D-isomer. It will also be understood that the terms DL-carnitine and DL-carnitine chloride are used interchangeably in the specification and the claims since they can be used interchangeably in the process of the invention unless otherwise specifically indicated. The same interchangeability is also used with respect to D- and L-carnitine and their corresponding chlorides.

The duration of the process may be from 24 hours to 5 days or more. The incubation temperature is usually from 25° to 37° C. The contents are suitably aerated with sterilized air and agitated to facilitate growth of the microorganism and thus enhance the effectiveness of the process.

Upon completion of the fermentation process, the desired L-carnitine is recovered by means well known in the art. For example, the fermentation liquor and cells can be first separated by conventional methods, e.g., filtration or centrifugation after which the fermentation liquor may be vacuum distilled to dryness. The resulting residue containing the desired L-carnitine may be extracted with anhydrous ethanol, the ethanolic extract evaporated to dryness in vacuo, and the L-carnitine converted into its hydrochloride salt by treating the residue with 6N HCl. After evaporation of the aqueous solution to dryness, L-carnitine chloride may be crystallized from a mixture of absolute ethanol-acetone. Alternatively L-carnitine inner salt may be obtained by chromatographing the residue of the ethanolic extract on a Dowex-1-OH ion exchange column [F. Strack and I. Lorenz, *Z. Physiol. Chemie* 318 (1960) 129].

It will be appreciated that, if desired, the cells of the microorganism may be immobilized [S. Fukui, A. Tanaka, Ann. Rev. of Microbiol. 1982, Vol. 36, p. 145] to permit the process to be carried out in a continuous manner. It will also be evident that to enhance stereoselectivity the growth medium may be modified or further mutagenisis of the mutant accomplished.

The following examples are to be considered illustrative only of the present invention and are not to be construed as limiting. Percentages are given by weight and solvent mixture proportions are expressed by volume unless otherwise stated. The isolated L-carnitine was characterized by proton magnetic resonance spectra, melting point, mobility on thin layer chromatography and optical rotation.

EXAMPLE 1

Isolation of the Wild Type (df-2) of *Acinetobacter calcoaceticus* ATCC 39648

*A. calcoaceticus* ATCC 39648 was isolated from a sewage sample obtained from a skimming tank using a selection medium via the following procedure:

Ten milliliters of greasy surface water from a sewerage skim tank (Nine Springs treatment plant, Madison, WI) was collected and 1 ml of this sample was added to a 250 ml Erlenmeyer flask containing 50 ml of modified Johnson's medium (Medium A):

| Medium A | |
|---|---|
| Yeast extract (Difco) | 50 mg |
| $KH_2PO_4$ | 5.5 g |
| $Na_2HPO_4$ | 10.0 g |
| $(NH_4)_2HPO_4$ | 2.0 g |
| $NH_4H_2PO_4$ | 1.5 g |
| $CaCl_2$ | 15 mg |
| $MgSO_4.7H_2O$ | 200 mg |
| $Fe_2(SO_4)_3$ | 0.6 mg |
| $ZnSO_4.7H_2O$ | 0.2 mg |
| $CuSO_4.5H_2O$ | 0.2 mg |
| $MnSO_4.H_2O$ | 0.2 mg |
| Deionized distilled water | 1 liter |

DL-carnitine HCl (Sigma) (10 g/l) is added and the pH is adjusted to 6.8 with 4N NaOH prior to sterilization at 121° C. for 20 minutes. The inoculated flask was incubated on a rotary shaker (250 rpm, 2" stroke, 27° C.). After 16 hours, one ml of the turbid broth was transferred to another flask containing like medium and reincubated on a rotary shaker for 16 hours. The procedure was repeated for a third time after which the turbid broth was diluted serially using M/15 phosphate buffer, pH 7.4. An aliquot (0.1 ml) of each dilution was spread evenly over the agar surface of a petri plate containing 1% of DL-carnitine chloride and 2% agar in modified Johnson's medium A. Different colony types were selected from plates that contained between 30 and 300 colonies per plate. The colonies were streaked on 1% DL-carnitine chloride modified Johnson's medium agar plates and checked for purity. The pure isolates were then tested for their ability to utilize D-carnitine and L-carnitine as a sole carbon source on modified Johnson's medium containing 0.5% of either D- or L-carnitine. It was observed that the isolate "df-2" grew considerably faster on D-carnitine than on L-carnitine. Hence this wild strain was chosen for the subsequent mutagenesis study.

EXAMPLE 2

PREPARATION OF MUTANT *A. CALCOACETICUS* ATCC 39647 FROM WILD TYPE "DF-2", *A. CALCOACETICUS* ATCC 39648

(a) *Nitrosoguanidine Mutagenesis*

The wild type "df-2", identified as *Acinetobacter calcoaceticus* (University Hospital Clinical Microbiology Laboratory, Madison, WI), was maintained on 1% DL-carnitine chloride modified Johnson's agar medium slants and stored at 4° C. A 250 ml Erlenmeyer flask containing 50 ml of 1% DL-carnitine chloride modified Johnson's medium was inoculated from a slant and then incubated for 16 hours on a rotary shaker (250 rpm, 2" stroke, 27° C.). To this overnight growth was added N-ethyl-N'-nitro-N-nitrosoguanidine (Aldrich) (NTG)

to a final concentration of 300 μg/ml of medium. The flask was placed back on the rotary shaker and incubated for exactly 30 minutes. It had been previously established that 300 μg NTG/ml medium for 30 minutes killed approximately 99.9% of viable cells. After 30 minutes exposure to NTG, the cells were centrifuged down (10,000 rpm, 15 minutes). The cell pellet was resuspended in 5 ml of modified Johnson's medium containing 1% DL-carnitine chloride. Two ml of this suspension was used to inoculate a 250 ml Erlenmeyer flask containing 50 ml of 1% DL-carnitine chloride modified Johnson's medium. After the flask was incubated on a rotary shaker (200 rpm, 27° C.) for 16 hours, the turbidity was determined on a Gilford UV-visible spectrophotometer (Model 240) by monitoring the absorbance at 600 nm. This data allowed the calculation of the proper dilution to be used for plating and mutant selection.

(b) Selection and isolation of mutant *A. calcoaceticus* ATCC 39647

Mutagenized cells, as described above, were serially diluted in M/15 phosphate buffer pH 7.4 and spread onto plates containing 1% DL-carnitine chloride modified Johnson's agar medium. After incubation at 28° C. for about four days, the resulting colonies were replicated on modified Johnson's agar medium A containing 0.5% L-carnitine or 0.5% D-carnitine.

Colonies which grew well on the D-carnitine plate but poorly on the L-carnitine plate were purified by streaking onto 0.5% D-carnitine modified Johnson's agar plates (medium A). After growth at 28° C., individual colonies were picked from the agar plates onto slants and then evaluated in shake flasks.

(c) Shake flask evaluation

Shake flasks (250 ml) containing 50 ml of 1% DL-carnitine chloride modified Johnson's liquid medium A were inoculated with several loops of cells taken from an agar slant. After 24 hours on a rotary shaker, 50 ml of this turbid broth served as the inoculum for another 2 L Erlenmeyer flask containing 500 ml of the same medium. After incubation at 27° C. on rotary shaker (250 rpm, 2" stroke) for 44 hours, 100 ml of the flask contents were evaporated to dryness in vacuo and the residue was extracted with absolute ethanol. The ethanolic extract was again evaporated to dryness in vacuo and the residue was dissolved in 10 ml of 6N HCl to convert carnitine into its chloride salt. The aqueous sample was then concentrated to dryness in vacuo and the residual L-carnitine chloride was crystallized from absolute ethanol-acetone. The high negative rotation of the product ($[\alpha]_D^{25} - 23.07°$ C. (c, 3.5 $H_2O$)) confirms the selective degradation of D-carnitine by the novel mutant produced from the parent wild strain *A. calcoaceticus* ATCC 39648.

*Acinetobacter Calcoaceticus* and the strains identified by ATCC 39647 and ATCC 39648 have the following properties:

Morphological Characteristics
  Medium—Difco nutrient agar (Difco Laboratories, Detroit, Mich.);
  Shape and size of cell—Rods 1–1.6 um in diameter and approximately 1.5–2.2 um in length;
  becoming spherical (coccoid rods) in the stationary phase of growth;
  often occur in pairs and in chains of variable length.
  No flagella.
  No spores.
  Gram negative.
  Non acid fast.
Culture Growth Condition
  Medium—Difco nutrient agar (Difco Laboratories, Detroit, Mich.)
  Colonies are relatively large (2–3 mm in 24 hrs.) are opaque and nonpigmented;
  Organism can grow in a simple mineral salts medium containing a single carbon energy source such as ethanol, acetate, lactate, pyruvate, malate or alpha-ketoglutarate;
  Ammonium salts serve as nitrogen sources;
  Gelatin not liquefied in gelatine stab culture and growth limited to top 3 mm of medium;
  Alkaline reaction in litmus milk with no coagulation or liquefaction and very poor growth.
Physiological Properties
  Nitrate reduction—negative
  Denitrification reaction—negative
  MR test—negative
  Indole production—negative
  VP test—negative
  Hydrogen sulfide production—very, very weak
  Starch hydrolysis—negative
  Utilization of citrate—positive
  Utilizes ammonium salts
  Pigment Production—yellowish intracellular water soluble pigment which is released into medium upon autolysis after 2–3 days.
  Urease—positive
  Oxidase—negative
  Catalase—positive
  Growth conditions
    pH 5–8.5
    temperature 5°–35° C.
    will not grow anaerobically in any medium.

| Production of acids and gas in following: | | | | |
|---|---|---|---|---|
| | ATCC 39648 | | ATCC 39647 | |
| | Open | Covered | Open | Covered |
| (1) L-arabinose | A | — | A | — |
| (2) D-xylose | A | — | A | — |
| (3) D-glucose | A | $A^\mu$ | A | — |
| (4) D-mannose | A | — | A | — |
| (5) D-fructose | $A^\mu$ | — | $A^\mu$ | — |
| (6) D-galactose | A | — | A | — |
| (7) maltose | — | — | — | — |
| (8) sucrose | — | — | — | — |
| (9) lactose | — | — | — | — |
| (10) trehalose | — | — | — | — |
| (11) D-sorbital | — | — | — | — |
| (12) D-mannitol | — | — | — | — |
| (13) inositol | — | — | — | — |
| (14) glycerine | — | — | — | — |
| (15) starch | — | — | — | — |

Key:
A = acid reaction
$\mu$ = weak reaction
— = no change or alkaline reaction

Other Characteristics
  Oxdizes ethyl alcohol;
  Has high tolerance for sodium chloride (2–3% NaCl);
  Can grow at 33° C.
  Phenylalanine is not deaminated;
  Lysine is not decarboxylated;
  Ornithine is not decarboxylated.

EXAMPLE 3

Isolation of the Wild Type (4d,1–3) of *Acinetobacter lwoffi* ATCC 39770

*A. lwoffi* ATCC 39770 was isolated from a sewage sample obtained from a skimming tank (Nine Springs treatment plant, Madison, Wis.) using the selection medium and procedure of Example 1. It was noted that this isolate (4d,1–3) grew considerably faster on D-Carnitine than on L-Carnitine. Hence this wild strain was chosen for the subsequent mutagenesis study.

EXAMPLE 4

Preparation of Mutant *A. lwoffi* ATCC 39769 from Wild Type "4d,1–3" *A. lwoffi* ATCC 39770

(a)

The wild type "4d,1–3," identified as *Acinetobacter lwoffi* (University Hospital Clinical Microbiology Laboratory, Madison, Wis.) was subjected to nitrosoguanidine mutagenesis and the mutant *A. lwoffi* ATCC 39769 was isolated according to the procedure outlined in Examples 2a and 2b.

(b) Shake Flask Evaluation.

The procedure of Example 2c was followed except that 2% DL-Carnitine chloride was used and the incubation period was extended to 72 hours. The high negative rotation of the product $9[\alpha]_D^{25} -20.5°$ (c, 2.0 H$_2$O) confirms the selective degradation of D-carnitine by the novel mutant produced from the parent wild strain *A. lwoffi* ATCC 39770.

*Acinetobacter lwoffi* ATCC 39769 and 39770

(1) Morphological Characteristics (Difco nutrient agar)
  (1) Rods 1–1.6 um in diameter and approximately 1.5–2.2 μm in length;
  (2) becoming spherical (coccoid rods) in the stationary phase of growth. They often occur in pairs and in chains of variable length;
  (3) no flagella;
  (4) no spores;
  (5) Gram-negative;
  (6) non-acid fast.
(2) Culture Growth Conditions
  Colonies are relatively large (2–3 mm in 24 hrs), are opaque and non-pigmented. Organism can grow in a simple mineral salts medium containing a single carbon and energy source such as ethanol, acetate, lactate, pyruvate, malate, or -ketoglutarate. Ammonium salts serve as nitrogen sources. Gelatin not liquefied in gelatin stab culture and growth limited to top 3 mm of medium; alkaline reaction in litmus milk with no coagulation or liquifaction and very poor growth.
(3) Physiological Properties
  (1) Nitrate reduction (negative);
  (2) denitrification reaction (negative);
  (3) MR test (negative);
  (4) VP test (negative);
  (5) indole production (negative);
  (6) starch hydrolysis (negative);
  (7) utilization of citrate (negative);
  (8) urease (negative);
  (9) oxidase (negative);
  (10) catalase (positive);
  (11) pH 5–8.5, temperature 5°–35° C.;
  (12) inability to grow anaerobically in any medium;
  (13) no acid production on the following carbohydrates:
    (1) L-arabinose
    (2) D-xylose
    (3) D-glucose
    (4) D-mannose
    (5) D-fructose
    (6) D-galactose
    (7) maltose
    (8) sucrose
    (9) lactose
    (10) trehalose
    (11) D-sorbitol
    (12) D-mannitol
    (13) inositol
    (14) glycerine
    (15) starch The strains of *A. lwoffi* which have the characteristics of ATCC 39769 and ATCC 39770 have been deposited with the American Type Culture Collection, 12301 Parklawn Drive, Rockville, Md. 20852.

EXAMPLE 5

Preferential Utilization of D-carnitine by *A. calcoaceticus* ATCC 39648

The surface growth from a one week old slant of *A. calcoaceticus* ATCC 39648 was suspended in 5 ml of saline (0.85%) solution. Two ml of this suspension were used to inoculate 50 ml of the modified Johnson's medium A containing 1% DL-carnitine chloride above held in a 250 ml Erlenmeyer flask (f-1 stage). The flask was incubated at 25° C. on a rotary shaker (250 rpm/min—2 inch radius) for 24 hours, after which a 10% by volume transfer was made to a two liter Erlenmeyer flask (F-2 stage), containing 500 ml of the same medium. After 12 hours on the rotary shaker, 100 ml of the medium was removed, centrifuged, and then evaporated to dryness in vacuo. The residue was extracted with hot ethanol and the ethanolic extract was concentrated to dryness in vacuo. The residue was dissolved in 10 ml of 6N HCl and the aqueous solution was concentrated to dryness. Crystallization of the residue from absolute ethanol-aetone afforded a sample of carnitine chloride (216 mg, 43% yield) ($[\alpha]_D^{25} -12.0°$) (c, 7.2 H$_2$O) indicating an enantiomeric excess (ee) of 0.51.

EXAMPLE 6

The surface growth from a one week old slant of *A. calcoaceticus* ATCC 39647 was suspended in 5 ml of medium A. Four ml of this suspension was used to inoculate 50 ml of the modified Johnson's medium A containing 1% DL-carnitine chloride above held in a 250 ml Erlenmeyer flask (F-1 stage). The flask was incubated at 25° C. on a rotary shaker (250 rpm/min—2 inch radius) for 24 hours, after which a 10% by volume transfer was made to a two liter Erlenmeyer flask (F-2 stage) containing 500 ml of the following medium (Medium B):

| Medium B | |
| --- | --- |
| Yeast extract (Difco) | 50 mg |
| KH$_2$PO$_4$ | 5.5 g |
| Na$_2$4PO$_4$ | 10.0 g |
| (NH$_4$)$_2$HPO$_4$ | 4.0 g |
| NH$_4$H$_2$PO$_4$ | 3.5 g |
| CaCl$_2$ | 15 mg |
| MgSO$_4$.7H$_2$O | 200 mg |
| Fe$_2$(SO$_4$)$_3$ | 0.6 mg |

-continued

| Medium B | |
|---|---|
| ZnSO$_4$.7H$_2$O | 0.2 mg |
| CuSO$_4$.5$_2$O | 0.2 mg |
| MnSO$_4$.H$_2$O | 0.2 mg |
| Deionized distilled water | 1 liter |

DL-Carnitine HCl (Sigma) (20 g/l) is added and the pH is adjusted to 6.8 with 4N NaOH prior to sterilization at 121° C. for 20 minutes.

After incubation for 44 hours on the rotary shaker at 25° C., 50 ml of the contents were centrifuged to remove the cells and the supernatant was then evaporated to dryness. L-carnitine chloride (196 mg, 38% yield) was isolated following the procedure described in Example 3. The optical purity was estimated to be greater than 96.5% ee from the $[\alpha]_D^{25} -22.9°$ (c, 2.65 H$_2$O) value.

EXAMPLE 7

The procedure of Example 4 was followed except that the concentration of DL-carnitine chloride for the F-2 stage was 50 g/l in a 250 ml Erlenmeyer flask containing 50 ml of the same medium. After the F-2 stage was allowed to proceed for 68 hours, L-carnitine chloride (180 mg, 42% yield) was isolated via the same procedure (Example 3) from 17 ml of the fermentation broth. The optical purity of the sample was greater than 86% ee as evidenced by the $[\alpha]_D^{25} -20.43°$ (c, 2.36 H$_2$O) value.

EXAMPLE 8

The procedure of Example 2c was followed except the 1% DL-carnitine chloride concentration consisted of a mixture of 0.3% L-carnitine chloride and 0.7% D-carnitine chloride in medium A. The fermentation was carried out in a 2 liter Erlenmeyer flask containing 250 ml of medium A using *A. calcoaceticus* ATCC 39647. After the F-2 stage was allowed to proceed for 44 hours, 100 ml of the broth was removed and the L-carnitine chloride isolated [36 mg (12% yield), $[\alpha]_D^{25} -21.2°$, c, 3.6, H$_2$O].

EXAMPLE 9

The procedure of Example 2c was followed except the 2% DL-carnitine chloride concentration consisted of a mixture of 1.6% of L-carnitine chloride and 0.4% of D-carnitine chloride in medium A using *A. calcoaceticus* ATCC 39647. After the F-2 stage was allowed to proceed for 44 hours, 100 ml of the broth was removed and the L-carnitine chloride isolated [551 mg (34% yield), $[\alpha]_D^{25} -23.05°$, c, 2.6, H$_2$O].

EXAMPLE 10

The procedure of Example 2c was followed except that the concentration of DL-carnitine chloride for the F-2 stage was 50 g/l, which consisted of 3 parts of L-carnitine chloride and 7 parts D-carnitine chloride in 250 ml of medium B held in a two liter Erlenmeyer flask. After incubation with *A. calcoaceticus* ATCC 39647 for 69 hours (F-2 stage), 50 ml of the broth was centrifuged (9000×6 for 20 minutes) to remove the cells. The supernatant was evaporated to dryness in vacuo and the residue was extracted with anhydrous ethanol. The ethanolic extract was concentrated to dryness and the residue was dissolved in distilled water and chromatographed over a Dowex 1-X-4 OH column (5×22 cm) to obtain L-carnitine [140 mg (23% yield), $[\alpha]_D^{25} -29.2°$, c, 1.5 H$_2$O].

EXAMPLE 11

The procedure of Example 8 was followed except that the concentration of DL-carnitine chloride for the F-2 stage was 50 g/l, which consisted of 8 parts of L-carnitine chloride and 2 parts of D-carnitine chloride. L-carnitine inner salt was isolated as before from 50 ml of the fermentation mixture (F-2 stage, 69 hours) [1.216 g (75% yield, $[\alpha]_D^{25} -30.4°$, c=2.8, H$_2$O].

EXAMPLE 12

The procedure of Example 8 was followed except that the concentration of DL-carnitine chloride for the F-2 stage was 50 g/l. After the F-2 stage was allowed to proceed for 90 hours, 40 ml of the fermentation broth was removed and centrifuged. L-carnitine inner salt was isolated as before [1.062 g (75% yield), $[\alpha]_D^{25} -27.0°$, c=4.4, H$_2$O].

What is claimed is:

1. A process for preparing L-carnitine and salts thereof which comprises subjecting a racemic mixture of DL-carnitine to the fermentative action of a microorganism selected from the family Neisseriaceae which is characterized by its unique ability to preferentially degrade the unnatural form of carnitine, D-carnitine, in said mixture and thereby permit the accumulation of the natural form of carnitine, L-carnitine, in the reaction medium and recovering the L-carnitine from said medium.

2. The process of claim 1 wherein the microorganism is selected from the genus Acinetobacter.

3. The process of claim 2 wherein the microorganism is a mutant of a strain of Acinetobacter.

4. The process of claim 2 wherein the microorganism has the characteristics of *Acinetobacter calcoaceticus* ATCC 39648.

5. The process of claim 3 wherein the microorganism has the characteristics of *Acinetobacter calcoaceticus* ATCC 39647.

6. The process of claim 3 herein the microorganism has the characteristics of *Acinetobacter lwoffi* ATCC 39769.

7. The process of claim 2 wherein the microorganism has the characteristics of *Acinetobacter lwoffi* ATTC 39770.

8. The process of claim 1 wherein the process is carried out in a growing culture of the microorganism in an aqueous nutrient medium under aerobic conditions.

9. The process of claim 1 wherein the process is effected by immobilized cells of the microorganism.

10. The process of claim 1 wherein the process is continuous.

11. The process of claim 1 wherein the process is carried out in a microorganism-free medium containing the enzymes elaborated by the microorganism.

12. The process of claim 1 wherein the process is carried out at a temperature in the range from about 25° C. to about 37° C.

13. The process of claim 1 wherein the process is carried out in a medium comprising mineral salts, mineral ions and DL-carnitine as the sole carbon source.

14. The process of claim 13 wherein the mineral salts medium is Johnson's Medium A.

15. The process of claim 13 wherein the mineral salts medium is Johnson's Medium B.

16. The process of claim 13 wherein the rate of metabolism of the D-isomer of carnitine is optimized by increasing the ammonium ion concentration in the reaction medium as the DL-carnitine concentration increases.

17. A process for resolving a racemic mixture of DL-carnitine which comprises
culturing a microorganism of the genus Acinetobacter, or a mutant of a strain of Acinetobacter, which is characterized by the unique ability to preferentially degrade the unnatural form of carnitine, D-carnitine, in an aqueous nutrient medium under aerobic conditions in the presence of a racemic mixture of DL-carnitine as the sole carbon source, whereby the D-carnitine in said racemic mixture is preferentially degraded.

18. The process of claim 17 wherein the microorganism is *Acinetobacter calcoaceticus* ATCC 39647.

19. The process of claim 17 wherein the microorganism is *Acinetobacter calcoaceticus* ATCC 39648.

20. The process of claim 17 wherein the microorganism is *Acinetobacter lwoffi* ATCC 39769.

21. The process of claim 17 wherein the microorganism is *Acinetobacter lwoffi* ATCC 39770.

22. Mutant strains of bacterium of the family Neisseriaceae which are characterized by their ability to resolve a racemic mixture of DL-carnitine by preferentially degrading the unnatural form of carnitine, D-carnitine, in the racemic mixture and permitting L-carnitine to accumulate.

23. Bacterium according to claim 22 selected from the genus Acinetobacter.

24. A bacterium according to claim 23 having the identifying characteristics of *Acinetobacter calcoaceticus* ATCC 39647.

25. The bacterium of claim 24 in freeze dried form.

26. A bacterium according to claim 22 having the identifying characteristics of *Acinetobacter lwoffi* ATCC 39769.

27. The bacterium of claim 26 in freeze dried form.

28. A biologically pure culture of a microorganism of the genus Acinetobacter which is capable of resolving a racemic mixture of DL-carnitine by preferentially degrading the unnatural form of carnitine, D-carnitine, in the racemic mixture.

29. A culture according to claim 28 wherein the microorganism is *Acinetobacter calcoaceticus* having the identifying characteristics of ATCC 39647.

30. The culture of claim 29 in freeze dried form.

31. A culture according to claim 28 wherein the microorganism is *Acinetobacter calcoaceticus* having the identifying characteristics of ATCC 39648.

32. The culture of claim 31 in freeze dried form.

33. A culture according to claim 28 wherein the microorganism is *Acinetobacter lwoffi* having the identifying characteristics of ATCC 39769.

34. The culture of claim 33 in freeze dried form.

35. A culture according to claim 28 wherein the microorganism is *Acinetobacter lwoffi* having the identifying characteristics of ATCC 39770.

36. The culture of claim 35 in freeze dried form.

* * * * *